(12) United States Patent
McGinley et al.

(10) Patent No.: US 10,893,873 B2
(45) Date of Patent: Jan. 19, 2021

(54) UNICORTAL PATH DETECTION FOR A SURGICAL DEPTH MEASUREMENT SYSTEM

(71) Applicant: McGinley Engineered Solutions, LLC, Casper, WY (US)

(72) Inventors: Joseph C. McGinley, Casper, WY (US); Vincent Palazzolo, Casper, WY (US); Adam M. Johnson, Casper, WY (US)

(73) Assignee: McGinley Engineered Solutions, LLC, Casper, WY (US)

(*) Notice: Subject to any disclaimer, the term of this patent is extended or adjusted under 35 U.S.C. 154(b) by 89 days.

(21) Appl. No.: 16/401,376

(22) Filed: May 2, 2019

(65) Prior Publication Data

US 2019/0254684 A1    Aug. 22, 2019

Related U.S. Application Data

(62) Division of application No. 15/334,841, filed on Oct. 26, 2016, now Pat. No. 10,321,921.

(60) Provisional application No. 62/247,025, filed on Oct. 27, 2015.

(51) Int. Cl.
*A61B 17/16* (2006.01)

(52) U.S. Cl.
CPC .......... *A61B 17/1626* (2013.01); *A61B 17/16* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628
See application file for complete search history.

(56) References Cited

U.S. PATENT DOCUMENTS

| | | | | |
|---|---|---|---|---|
| 1,831,813 A | * | 11/1931 | Levedahl | ................ B23B 49/02 408/81 |
| 2,883,891 A | * | 4/1959 | Robinson | ................ B25F 5/003 408/112 |
| 3,804,544 A | | 4/1974 | Adams | |
| 4,014,621 A | | 3/1977 | Johnson et al. | |
| 4,063,356 A | | 12/1977 | Hepworth | |
| 4,157,231 A | * | 6/1979 | Phillips | ................ E21B 19/086 408/1 R |
| 4,310,269 A | * | 1/1982 | Neu | ........................ B23B 47/32 408/10 |

(Continued)

FOREIGN PATENT DOCUMENTS

DE    102011056927    6/2017
WO        9724991    7/1997

(Continued)

*Primary Examiner* — Eric S Gibson
(74) *Attorney, Agent, or Firm* — Holzer Patel Drennan

(57) ABSTRACT

Unicortical path detection for a measurement system for monitoring a depth of penetration of a working portion of an instrument in a bone of a patient. The unicortical detection may compare an average cortex thickness in a bicortical path to an actual measured depth of penetration. If the actual depth of penetration exceeds the average thickness, a unicortical path may be detected. Upon detection of a unicortical path, an alert may be provided and/or the instrument may be arrested upon subsequent breaching of the cortex.

6 Claims, 2 Drawing Sheets

(56) References Cited

U.S. PATENT DOCUMENTS

| | | | |
|---|---|---|---|
| 4,329,092 A * | 5/1982 | Ponitzsch | B23B 45/04 408/10 |
| 4,329,095 A * | 5/1982 | Schmuck | B23B 49/006 408/112 |
| 4,644,335 A * | 2/1987 | Wen | G01H 1/003 340/680 |
| 4,710,075 A | 12/1987 | Davison | |
| 4,723,911 A | 2/1988 | Kurtz | |
| 4,765,333 A | 8/1988 | Bray | |
| 4,867,158 A | 9/1989 | Sugg | |
| 4,951,690 A | 8/1990 | Baker | |
| 5,013,194 A | 5/1991 | Wienhold | |
| 5,014,793 A * | 5/1991 | Germanton | B25B 21/00 173/181 |
| 5,022,798 A | 6/1991 | Eckman | |
| 5,071,293 A * | 12/1991 | Wells | B23Q 5/263 408/112 |
| 5,133,728 A | 7/1992 | Petersen | |
| 5,139,376 A | 8/1992 | Pumphrey | |
| 5,161,921 A | 11/1992 | Corsi | |
| 5,277,799 A | 1/1994 | Bransch | |
| 5,361,504 A | 11/1994 | Huang | |
| 5,380,333 A | 1/1995 | Meloul et al. | |
| 5,411,503 A * | 5/1995 | Hollstien | A61B 17/1707 606/80 |
| 5,533,842 A * | 7/1996 | Johnson | B23Q 5/265 408/130 |
| 5,538,423 A * | 7/1996 | Coss | A61C 1/0015 408/8 |
| 5,584,838 A * | 12/1996 | Rona | A61B 17/1707 324/226 |
| 5,599,142 A * | 2/1997 | Fujimoto | B23Q 15/12 408/10 |
| 5,613,810 A * | 3/1997 | Bureller | B23Q 15/12 408/11 |
| 5,810,828 A * | 9/1998 | Lightman | A61B 17/164 606/80 |
| 5,902,306 A | 5/1999 | Norman | |
| 5,961,257 A * | 10/1999 | Bettini | E01B 31/24 408/97 |
| 5,980,248 A * | 11/1999 | Kusakabe | A61C 1/0007 433/131 |
| 6,033,409 A * | 3/2000 | Allotta | A61B 17/1622 606/170 |
| 6,081,741 A | 6/2000 | Hollis | |
| 6,096,042 A * | 8/2000 | Herbert | B23B 49/006 606/80 |
| 6,342,057 B1 | 1/2002 | Brace et al. | |
| 6,494,590 B1 * | 12/2002 | Paganini | B25F 5/021 362/109 |
| 6,527,778 B2 * | 3/2003 | Athanasiou | A61B 10/0233 606/80 |
| 6,587,184 B2 | 7/2003 | Wursch et al. | |
| 6,665,948 B1 * | 12/2003 | Kozin | A61B 17/1626 175/45 |
| 6,786,683 B2 * | 9/2004 | Schaer | B23B 49/006 408/16 |
| D502,798 S | 3/2005 | Belley et al. | |
| 6,925,725 B2 * | 8/2005 | Herrmann | B21J 15/10 33/638 |
| 7,073,989 B2 * | 7/2006 | Erickson | B23B 45/003 408/112 |
| 7,185,998 B2 * | 3/2007 | Oomori | B25B 23/18 362/119 |
| 7,220,088 B2 | 5/2007 | Ferrari et al. | |
| 7,235,940 B2 * | 6/2007 | Bosch | B25B 23/147 173/4 |
| 7,314,048 B2 | 1/2008 | Couture et al. | |
| 7,482,819 B2 * | 1/2009 | Wuersch | B23B 49/006 173/6 |
| 7,578,642 B2 * | 8/2009 | Fritsche | B23Q 1/28 227/110 |
| 7,681,659 B2 * | 3/2010 | Zhang | B25B 21/00 173/1 |
| 7,691,106 B2 | 4/2010 | Schenberger | |
| 7,946,049 B1 * | 5/2011 | Wilton | E04F 21/0092 33/526 |
| 7,992,311 B2 * | 8/2011 | Cerwin | B25H 1/0092 33/286 |
| 8,092,457 B2 | 1/2012 | Oettinger | |
| 8,162,074 B2 * | 4/2012 | Cook | B25F 5/021 173/1 |
| 8,167,518 B2 * | 5/2012 | Mathis | B23Q 5/225 408/1 R |
| 8,171,642 B2 * | 5/2012 | Fritsche | B23Q 1/621 29/897.2 |
| 8,317,437 B2 * | 11/2012 | Merkley | G05B 19/4163 408/9 |
| 8,460,297 B2 | 6/2013 | Watlington | |
| 8,511,945 B2 | 8/2013 | Apkarian | |
| 8,734,153 B2 * | 5/2014 | Arzanpour | A61C 1/0007 433/114 |
| 8,821,493 B2 * | 9/2014 | Anderson | A61B 90/06 606/80 |
| 8,894,654 B2 * | 11/2014 | Anderson | B25B 21/002 606/80 |
| 8,925,169 B2 * | 1/2015 | Schevers | B23B 49/00 29/407.08 |
| 8,970,207 B2 * | 3/2015 | Baumgartner | G01D 5/145 324/207.2 |
| 9,022,949 B2 | 5/2015 | Herndon | |
| 9,114,494 B1 * | 8/2015 | Mah | B25H 1/0092 |
| 9,204,885 B2 * | 12/2015 | McGinley | A61B 17/162 |
| 9,358,016 B2 * | 6/2016 | McGinley | A61B 17/1628 |
| 9,370,372 B2 * | 6/2016 | McGinley | A61B 17/162 |
| 9,492,181 B2 * | 11/2016 | McGinley | A61B 17/162 |
| 9,826,984 B2 | 11/2017 | McGinely | |
| 2001/0047219 A1 * | 11/2001 | Oden | B23Q 17/12 700/159 |
| 2002/0165549 A1 | 11/2002 | Owusu-Akyaw et al. | |
| 2003/0049082 A1 * | 3/2003 | Morrison | B23B 49/026 408/56 |
| 2003/0229351 A1 | 12/2003 | Tidwell | |
| 2004/0146367 A1 * | 7/2004 | Gerhardt | B25F 5/003 408/110 |
| 2004/0179829 A1 * | 9/2004 | Phillips | H02P 29/02 388/804 |
| 2004/0215395 A1 * | 10/2004 | Strasser | B23B 49/006 702/9 |
| 2005/0116673 A1 * | 6/2005 | Carl | A61B 17/1626 318/432 |
| 2005/0131415 A1 * | 6/2005 | Hearn | A61B 17/8875 606/80 |
| 2005/0169717 A1 * | 8/2005 | Field | E21B 47/04 408/13 |
| 2005/0261870 A1 * | 11/2005 | Cramer | B25H 1/0092 702/166 |
| 2006/0004371 A1 | 1/2006 | Williams et al. | |
| 2006/0008771 A1 * | 1/2006 | Courvoisier | A61B 17/1615 433/165 |
| 2006/0025677 A1 | 2/2006 | Verard | |
| 2006/0241628 A1 | 10/2006 | Parak | |
| 2006/0258938 A1 | 11/2006 | Hoffman | |
| 2007/0030486 A1 * | 2/2007 | Gelbart | G01B 11/27 356/399 |
| 2007/0035311 A1 * | 2/2007 | Wuersch | B23B 49/006 324/644 |
| 2007/0041799 A1 | 2/2007 | Schaefer | |
| 2008/0119725 A1 | 5/2008 | Lloyd | |
| 2008/0167653 A1 | 7/2008 | Watlington | |
| 2008/0226409 A1 | 9/2008 | Hasenzahl | |
| 2008/0243125 A1 | 10/2008 | Guzman | |
| 2008/0292416 A1 | 11/2008 | Kado et al. | |
| 2009/0131986 A1 | 5/2009 | Lee et al. | |
| 2009/0182226 A1 | 7/2009 | Weitzner | |
| 2009/0245956 A1 * | 10/2009 | Apkarian | A61B 34/30 408/1 R |
| 2009/0299439 A1 * | 12/2009 | Mire | A61B 17/1671 607/60 |

(56) References Cited

U.S. PATENT DOCUMENTS

| | | | |
|---|---|---|---|
| 2009/0326537 A1* | 12/2009 | Anderson | A61B 17/17 606/80 |
| 2010/0114099 A1 | 5/2010 | Patwardhan | |
| 2010/0137874 A1* | 6/2010 | Kim | G01B 3/28 606/102 |
| 2010/0239380 A1 | 9/2010 | Amirov et al. | |
| 2011/0060242 A1* | 3/2011 | Hausman | A61B 17/1626 600/554 |
| 2011/0245831 A1 | 10/2011 | Giersch et al. | |
| 2011/0245832 A1 | 10/2011 | Giersch et al. | |
| 2011/0245833 A1* | 10/2011 | Anderson | B23B 45/008 606/80 |
| 2011/0301611 A1* | 12/2011 | Garcia | B25B 23/147 606/80 |
| 2012/0037386 A1* | 2/2012 | Cook | B25F 5/021 173/30 |
| 2012/0123418 A1 | 5/2012 | Giurgi | |
| 2012/0179070 A1 | 7/2012 | Pommer et al. | |
| 2012/0253348 A1 | 10/2012 | Arlettaz et al. | |
| 2013/0304069 A1* | 11/2013 | Bono | A61B 17/1624 606/80 |
| 2013/0307529 A1* | 11/2013 | Baumgartner | B23B 49/00 324/207.2 |
| 2013/0327552 A1 | 12/2013 | Lovelass | |
| 2014/0081659 A1 | 3/2014 | Nawana | |
| 2014/0107471 A1* | 4/2014 | Haider | A61B 1/3132 600/424 |
| 2014/0275760 A1 | 9/2014 | Lee | |
| 2014/0275989 A1 | 9/2014 | Jacobsen | |
| 2014/0350685 A1 | 11/2014 | Bagga | |
| 2015/0066030 A1* | 3/2015 | McGinley | A61B 17/1628 606/79 |
| 2015/0066035 A1* | 3/2015 | McGinley | A61B 90/30 606/80 |
| 2015/0066036 A1* | 3/2015 | McGinley | A61B 17/162 606/80 |
| 2015/0066037 A1* | 3/2015 | McGinley | A61B 17/16 606/80 |
| 2015/0066038 A1* | 3/2015 | McGinley | A61B 17/1615 606/80 |
| 2015/0165580 A1* | 6/2015 | Holland | B25F 5/021 408/1 BD |
| 2016/0120553 A1 | 5/2016 | Xie | |
| 2017/0128081 A1 | 5/2017 | McGinley | |
| 2017/0143396 A1* | 5/2017 | McGinley | A61B 17/16 |
| 2017/0245868 A1 | 8/2017 | McGinley | |
| 2017/0345398 A1 | 11/2017 | Fuchs | |
| 2018/0070113 A1 | 3/2018 | Phillips | |
| 2018/0110572 A1 | 4/2018 | Flatt | |
| 2018/0260931 A1 | 9/2018 | Ozguner | |
| 2019/0209287 A1 | 7/2019 | Zens-Olson | |
| 2019/0254684 A1* | 8/2019 | McGinley | A61B 17/16 |

FOREIGN PATENT DOCUMENTS

| | | |
|---|---|---|
| WO | 2015006296 | 1/2015 |
| WO | 2015014771 | 2/2015 |
| WO | 2015034562 | 3/2015 |
| WO | 2016207628 A1 | 12/2016 |

* cited by examiner

BICORTICAL DRILL PATH

UNICORTICAL DRILL PATH

UNICORTAL PATH DETECTION FOR A SURGICAL DEPTH MEASUREMENT SYSTEM

RELATED APPLICATIONS

This application is a Divisional of U.S. application Ser. No. 15/334,841, filed on Oct. 26, 2018, entitled "UNICORTAL PATH DETECTION FOR A SURGICAL DEPTH MEASUREMENT SYSTEM," which claims the benefit of U.S. Provisional Patent Application No. 62/247,025 filed Oct. 27, 2015, entitled "UNICORTAL PATH DETECTION FOR A SURGICAL DEPTH MEASUREMENT SYSTEM," which is incorporated herein by reference in its entirety.

FIELD

The present disclosure relates to instruments for use in surgical operations, namely operations relative to a bone of the patient.

BACKGROUND

Systems have been proposed that may determine when a leading edge of a working portion of an instrument is advanced from a first medium to a second medium. Such systems may utilize sensors to monitor conditions associated with the advancement of the working portion to automatically determine when the leading edge passes from the first medium to the second medium. For example, U.S. Pat. No. 6,665,948, which is incorporated by reference herein, describes one such system.

SUMMARY

In view of the foregoing, it has presently been recognized that additional safety measures may be utilized in conjunction with measurement systems that monitor advancement of a working portion of an instrument relative to anatomy of a patient. For instance, a measurement system may determine when the leading edge of the working portion of an instrument passes from a first medium to a second medium. The first medium may have a first density greater than a second medium having a second density. In turn, monitoring of the leading edge as it passes from a first medium to a second medium may be utilized to determine the position of the working portion as it is advanced through a bone of the patient (e.g., with respect to the various anatomical structures of a bone). In this regard, operation of the instrument and/or measurement system may depend upon whether the working portion is to follow a unicortical or bicortical path through a bone.

Specifically, when following a unicortical path, an instrument may be arrested or an alert may be generated upon the first occurrence of the leading edge of the working portion of the instrument passing from the first medium to the second medium. In contrast, when following a bicortical path, the leading edge of the working portion of the instrument may pass from a first portion of the hard outer cortex of the bone into an inner medullary layer (i.e., a first occurrence of the leading edge passing from a first medium having a higher density than a second medium), from the inner medullary layer into a second portion of the hard outer cortex, and then passing from the second portion of the hard outer cortex to the exterior of the bone (i.e., a second occurrence of the leading edge passing from a first medium having a higher density than a second medium).

Such a measurement system that monitors the advancement of a working portion of an instrument may be used in a number of contexts. For instance, the measurement system may be used to capture of the depth of the path that the working portion has traveled when passing through the bone. In other approaches, the occurrence may be used to arrest the instrument. In this approach, the instrument may be stopped to prevent the working portion from causing damage to anatomic structures exterior to the bone once the working portion has passed through the bone. That is, if the instrument is not stopped once it has passed entirely through the bone, the working portion may damage surrounding structures adjacent to the bone. In any regard, it may be necessary to accurately determine when the working portion has passed through the bone.

However, in the proposed approaches, a surgeon may determine whether a unicortical or bicortical path is to be followed. However, the path actually followed may be different than that anticipated by the surgeon or set in the measurement system. That is, the working portion may actually follow an unintended path that may differ from the operational mode of the instrument. For instance, where the instrument is operating in a bicortical mode, yet the actual path of the working portion takes a unicortical path (e.g., due to misalignment of the working portion, etc.), sensing the working portion pass from the first medium to the second medium at the first occurrence may not result in any arresting or alerting in the instrument. That is, in normal bicortical operation this first occurrence may correspond to the passing from the hard outer cortex to the inner medullary layer such that normally no action is taken. However, if the actual path followed is a unicortical path, this first occurrence of the working portion passing from the first medium to the second medium may actually correspond to the working portion breaching the exterior of the bone such that continued operation of the instrument once the working portion passes from the first medium to the second medium (i.e., from the hard outer cortex to the exterior of the bone) may result in unintended operation of the instrument.

As such, the present disclosure describes unicortical path detection that may be used to determine that an inadvertent unicortical path has been taken. In turn, bicortical operation may be overridden and an alert and/or arresting of the instrument may occur in the case of inadvertent unicortical operation. This may provide a safeguard in instances where instrument alignment may be difficult or other conditions exist where an intended bicortical path is actually unicortical.

Specifically, the present disclosure involves an average cortex thickness value. Specifically, the average cortex thickness value may be a predetermined value that is stored in memory and accessible by a controller of an instrument employing a measurement system. In turn, the controller may monitor a depth of penetration of the leading edge of a working portion and compare the measured depth to the average cortical thickness value. If the actual measured depth exceeds the average cortical thickness value, the controller may alert the user and/or arrest the instrument at the first occurrence of the leading edge passing from a first medium into a second medium having a lower density than the first medium. That is, the controller may override the bicortical operation of the instrument if the actual measured depth of penetration exceeds the average cortex thickness value.

In an embodiment described herein, the average cortex thickness value may be correlated to a bone type. For instance, different bone types may have different respective average cortex thicknesses. As such, different predetermined average cortex thickness values may be provided in corresponding relation to different bone types. Prior to initiating operation of the instrument, a bone type selection may be used to indicate the type of bone with which the instrument is to be used. In turn, a corresponding average cortex thickness value may be retrieved for the bone type selected and used to determine if an inadvertent unicortical path is taken. As such, variations in average cortical thickness in various bone types may be accounted for as potential for inadvertent unicortical operation may exist in a variety of bone types.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1A:
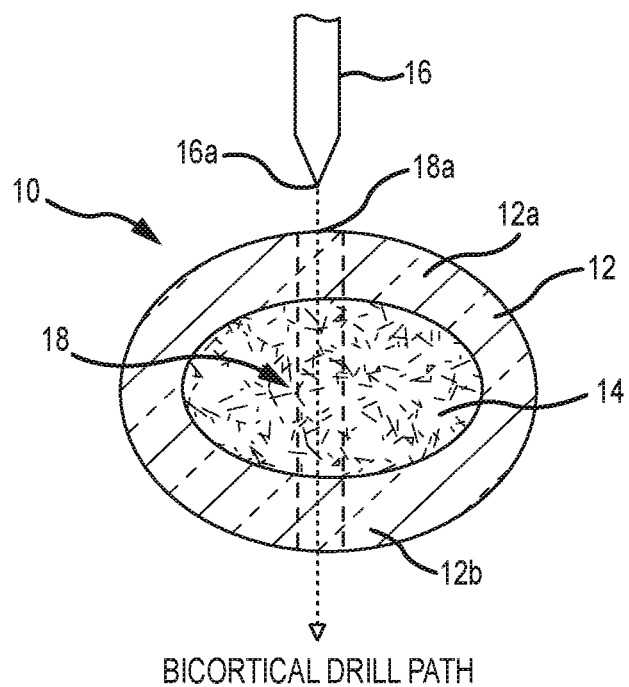
FIG. 1A is a cross sectional view of a bone of a patient where a bicortical path is defined.
Figure 1B:
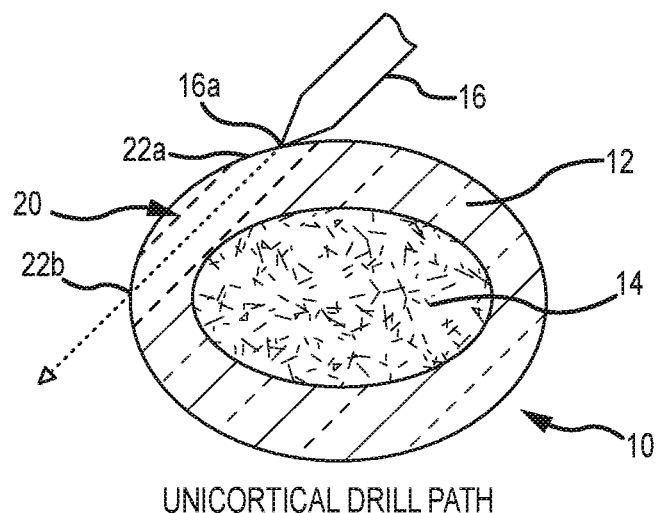
FIG. 1B is a cross sectional view of a bone of a patient where a unicortical path is defined.

As shown in FIGS. 1A and 1B, the bony structure of the human anatomy consists mainly of cortical bone 10 having a hard outer cortex 12 and a soft inner medullary layer 14. As shown in FIG. 1A, when advancing a working portion 16 of an instrument on a bicortical path 18 through the cortical bone 10, the working portion 16 passes through a first portion 12a of the hard outer cortex 12, a soft non-resistant medullary layer 14, and a second portion 12b of the hard outer cortex 12.

As shown in FIG. 1B, when using a working portion 16 to advance on a unicortical path 20 through the cortical bone 10, the working portion 16 passes through an entry point 22a of the hard outer cortex 12 and an exit point 22b of the hard outer cortex 12 without penetrating the soft non-resistant medullary layer 14.

Given that an instrument working portion 16 may pass through different structures depending upon whether traveling on a unicortical path or a bicortical path, an instrument having a measurement system may have different logic for determining when the working portion of the instrument has passed through the bone. For example, U.S. Pat. No. 6,665, 948, which is incorporated by reference above, includes a mode selection switch that allows for operation in a unicortical or a bicortical mode. In unicortical mode, the first occurrence of the instrument working portion 16 passing from a first medium having a first density to a second medium having a second density less than the first density may trigger the output of a signal indicative that the bone has been completely passed through. That is, the first occurrence of when the working portion 16 passes from the first medium to the second medium may correspond to the working portion 16 exiting the cortex at the exit point 22b of the bone.

However, in bicortical operation, the second occurrence of a determination that the working portion 16 has passed from a first medium having a first density greater than the second density may be used to generate a signal indicative that the bone has been completely passed through. That is, the first occurrence may occur when the working portion 16 passes from the first portion of cortex 12a into the medullary layer 14. As such, the instrument may continue to operate beyond the first occurrence. In turn, if the actual operation differs than the mode selected, disregarding the first occurrence may cause the disadvantages described above.

While the '948 Patent describes use of a force sensor and a displacement sensor for determining when the working portion 16 passes from a first medium to a second medium, the disclosure presented herein may be utilized with any manner of such cortical edge detection. For instance, U.S. application Ser. No. 14/845,602, which is incorporated by reference herein, discloses use of a single sensor (e.g., a displacement sensor alone or an accelerometer alone) to determine displacement, velocity, and acceleration signals that may in turn be used to determine cortical edges. The present application may also be used in this context. Furthermore, any appropriate processing used to determine when a cortical edge has been breached may benefit from use of an approach as described herein.

Specifically, it may be appreciated that the potential exists for a unicortical path to be taken during operation in a bicortical mode. Such a deviation from the intended path may result from misalignment of the working portion, which may occur due to difficult positioning of working portion due to anatomy or other considerations. Other times, the bone may be relatively small such that aligning the working portion for bicortical operation is difficult to achieve. In any regard, in the case where a unicortical path is taken during bicortical operation of the instrument, an incorrect or incomplete depth measurement process may occur or the instrument may not be properly arrested upon penetration of the cortex such that adjunct tissue may be damaged.

Figure 2:
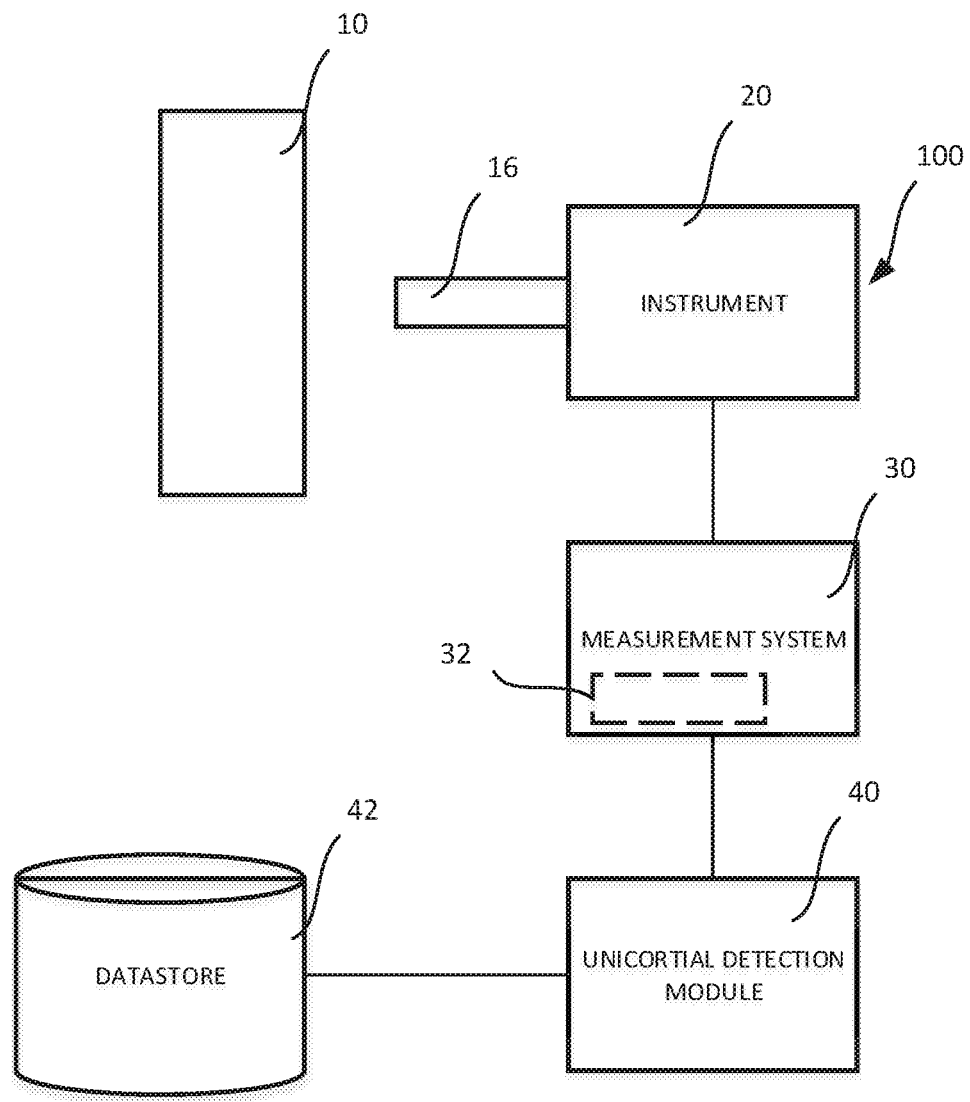
FIG. 2 is a schematic view of an embodiment of a system for unicortical detection.

With reference to FIG. 2, a system 100 is depicted that may be used to detect unintentional unicortical operation. The system 100 includes an instrument 20 for powering a working portion 16. As described above, the working portion 16 may be advanceable into a bone 10 of a patient. The instrument 20 may be a drill, saw, reamer, grinder, pin driver, or any other appropriate instrument for powering a corresponding working portion 16. As such, the working portion 16 may be drill bit, pin, wire, saw, reamer, grinding burr, or any other appropriate working portion 16 used in surgical operations.

The instrument 20 may be in operative communication with a measurement system 30. As described above, the measurement system 30 may be any appropriate system that may be used to determine when the working portion 16 passes from a first medium having a first density to a second medium having a second density. For example, the measurement system 30 may be used to sense when the working portion 16 passes from a portion of hard cortex 12a to an inner medullary layer 14 and/or when the working portion 16 passes from the hard cortex 12 to an exterior material surrounding the bone 10.

The measurement system 30 may have a controller 32. The controller 32 may be used to command operation of the measurement system 30. In this regard, the controller 32 may include a processor that is operative to access a memory storing machine readable instructions for configuration of the processor to achieve the functionality described herein. The controller 32 may include a user interface having a display and/or input devices operative to display information to a user and receive inputs from the user. As such, operational status information of the instrument 20 or measurement system 30 may be displayed to the user. For example, alarms may be displayed to the user. Moreover, control outputs for controlling operation of the instrument 20 or measurement system 30 may be provided from the controller 32. For instance, the controller 32 may output an alarm upon detection of a unicortical path during bicortical operation of the instrument 20. Moreover, the controller 32 may control the instrument 20 to arrest the instrument 20. This may occur when a unicortical path is detected or may occur when the measurement system 30 detects the working portion 16 has passed from a first medium to a second medium after detecting a unicortical path (e.g., once the working instrument 16 breaches the cortex 12).

As shown in FIG. 2, the system 100 may include a unicortical detection module 40. The unicortical detection module 40 may be in operative communication with the measurement system 30. Regardless of the specific approach used to monitor the working portion 16, the unicortical detection module 40 may interface with a displacement sensor of the measurement system 30 to determine an actual depth of penetration of the working portion 16 into the bone 10. As may be appreciated with further review of FIG. 1, the thickness of the first portion of hard cortex 12a in a bicortical path 18 may be less than the thickness of hard cortex 12 that the working portion 16 passes through in a unicortical path 20. That is, if the instrument working portion 16 progresses on a unicortical path 20, the distance the working portion 16 travels through the cortex 12 may be greater than the thickness of the first portion of hard cortex 12a though which the working portion 16 would pass in a bicortical path 18.

Accordingly, the unicortical detection module 40 may also be in operative communication with a datastore 42. The datastore 42 may store a predetermined average cortex thickness value. The average cortex thickness value may correspond to an average thickness of the first portion 12a of the cortex of a bicortical path 18. In turn, the unicortical detection module 40 may retrieve the average cortex thickness value for the bone 10 and compare the depth of penetration of the working portion 16 into the bone to the average cortex thickness value. If the actual depth of penetration of the working portion 16 exceeds the predetermined average cortex thickness value, a unicortical path may be detected and the controller 32 may control operation of the instrument 10 as described above. The predetermined average cortex thickness value may be slightly greater than an actual average value, thus allowing for factoring some bones with unusually thick cortices. Moreover, the unicortical detection module 40 may only detect unicortical operation if the actual depth of penetration exceeds the predetermined average cortex thickness value by a given value (e.g., 10% of the average thickness value).

Moreover, it may be appreciated that the average cortex thickness value may vary with different bone types. Accordingly, the datastore 42 may store average cortex thickness values for a plurality of bone types. In turn, the controller 32 may include a selection presented to a user that allows the user to indicate the type of bone in which the working portion 16 is to be advanced. Using the indication of bone type provided by the user, the unicortical detection module 40 may retrieve a corresponding given one of the predetermined average cortex thickness values for use in comparison to the depth of penetration for determining whether a unicortical path 20 is detected. For instance, a plurality of bone types may be selectable via the user interface of the controller 32 that each have a corresponding predetermined average cortex thickness value in the datastore 42. The bone types may include a femur/tibia type, a humerus type, a fibula type, a radius/ulna type, a pedicle type, a metacarpal/metatarsal/carpal/tarsal type, a phalanges type, a clavicle type. In addition to the selection of a bone type with a corresponding predetermined average cortex thickness value, the controller 32 may be able to accept an average cortex thickness value from a user prior to commencing operation.

As stated above, upon detection of a unicortical path 18, the unicortical detection module 40 may output an alarm and/or arrest the instrument at either the time the detection occurs or at the next subsequent occurrence of the working portion 16 passing from a first medium into a second medium. The controller 32 may also have the capability to override the alarm and/or arresting of the instrument 10. For example, after alarming/arresting, the user may determine that it is safe to continue with the operation of the instrument 10 and override the alarm/arresting to allow for continued operation of the instrument 10.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A method for control of an instrument having a working portion advanced into a bone of a patient, the method comprising:
   selecting a bone type of the bone in which the working portion is to be advanced;
   retrieving a predetermined average cortex thickness value corresponding to the bone type;
   monitoring a depth of penetration of the working portion into the bone of the patient;
   comparing the depth of penetration of the working portion into the bone of the patient to the predetermined average cortex thickness value;
   determining that the depth of penetration of the working portion exceeds the predetermined average cortex thickness value; and
   arresting the instrument, after the determining, upon sensing penetration of the working portion from a first medium having a first density to a second medium having a second density.

2. The method of claim 1, wherein the selecting comprises choosing the bone type from a plurality of bone types, wherein each of the plurality of bone types is correspondingly associated with a unique predetermined average cortex thickness.

3. The method of claim 2, wherein the plurality of bone types are selected from the group consisting of: a femur/tibia type, a humerus type, a fibula type, a radius/ulna type, a pedicle type, a metacarpal/metatarsal/carpal/tarsal type, a phalanges type, a clavicle type, and combinations thereof.

4. The method of claim 1, further comprising:
   alerting a user that the instrument is arrested.

5. The method of claim 4, further comprising:
   receiving an override of the alerting from the user; and restarting the instrument for further advancement of the working portion into the bone of the patient.

6. The method of claim 1, further comprising:

alerting the user that the depth of the penetration of the working portion exceeds the predetermined average cortex thickness value prior to the arresting.

\* \* \* \* \*